United States Patent

Bartels-Keith et al.

[11] 4,003,910
[45] Jan. 18, 1977

[54] MESO-IONIC SE- AND S-CONTAINING TETRAZOLES

[75] Inventors: James R. Bartels-Keith, Lexington; Mary T. Burgess, Boston, both of Mass.

[73] Assignee: Polaroid Corporation, Cambridge, Mass.

[22] Filed: Aug. 18, 1975

[21] Appl. No.: 605,401

[52] U.S. Cl. .......................................... 260/308 D
[51] Int. Cl.² ..................................... C07D 257/04
[58] Field of Search ............................... 260/308 D

[56] References Cited
FOREIGN PATENTS OR APPLICATIONS
1,037,176  8/1958  Germany ...................... 260/308 B

*Primary Examiner*—Frederick E. Waddell
*Attorney, Agent, or Firm*—Sybil A. Campbell

[57] ABSTRACT

This invention relates to meso-ionic tetrazole compounds of the formula:

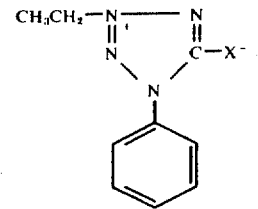

wherein $X^-$ is $-S^-$ or $-Se^-$ which are useful as photographic additives and to an intermediate useful in the preparation thereof having the formula:

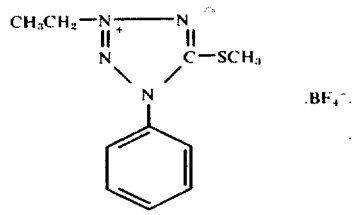

8 Claims, No Drawings

MESO-IONIC SE- AND S-CONTAINING TETRAZOLES

BACKGROUND OF THE INVENTION

1. Field of the Invention

This invention relates to novel meso-ionic sulfur- and selenium-containing tetrazole compounds useful in photography and to a novel intermediate useful in the preparation of said meso-ionic compounds.

2. Description of the Prior Art

Various tetrazolium compounds, i.e., quaternized tetrazoles containing a ring of one carbon and four nitrogren atoms, one of which is quaternary, are known. Though most of the tetrazolium salts prepared so far have been derived from (2H)tetrazoles, some quaternary salts of (1H)tetrazoles also have been reported. As discussed in Heterocyclic Compounds, Robert C. Elderfield, Vol. 8, pp. 55 and 62, John Wiley & Sons, Inc., New York, 1967, quaternization of 1,5-disubstituted tetrazoles occurs readily with methyl benzenesulfonate or methyl iodide to give the corresponding 4-methyl product in the quaternary salts investigated. For example, methylation of 1-methyl-5-methylthiotetrazole gave the corresponding 1,4-dimethyl-5-methylthiotetrazolium iodide. Like the tetrazolium salts, the meso-ionic tetrazole compounds previously reported have been primarily (2H)tetrazole derivatives.

The present invention is concerned with the ethylation of 1-phenyl-5-methylthiotetrazole, with the ethylation product obtained and with the products obtained upon solvolysis of the ethylation product with $^-$SeH and $^-$SH.

SUMMARY OF THE INVENTION

It is one object of the present invention to provide meso-ionic sulfur- and selenium-containing tetrazole compounds useful as photographic additives.

It is another object of this invention to provide a novel tetrazolium salt of a (1H)tetrazole useful as an intermediate in the preparation of said meso-ionic compounds.

It is still another object of this invention to provide a method of preparing said meso-ionic compounds and of preparing said intermediate.

Other objects of this invention will in part be obvious and will in part appear hereinafter.

The invention accordingly comprises the several steps and the relation and order of one or more such steps with respect to each of the others, and the products and compositions possessing the features, properties and the relation of elements, which are exemplified in the following detailed disclosure, and the scope of the application which will be indicated in the claims.

For a fuller understanding of the nature and object of the invention, reference should be had to the following detailed description.

DESCRIPTION OF THE PREFERRED EMBODIMENTS

According to the present invention, it has been found quite unexpectedly that ethylation occurs in the 3-position when 5-methylthio-1-phenyltetrazole is reacted with triethyloxonium fluoroborate. Also, it has been found that the 3-methyl-5-methylthio-1-phenyl tetrazolium fluoroborate thus obtained may be react with NaHS or with NaHSe to yield the corresponding 5-S$^-$ and 5-Se$^-$ meso-ionic tetrazole compounds, respectively.

Specifically, the novel meso-ionic tetrazole compounds provided by the present invention may be represented by the formula

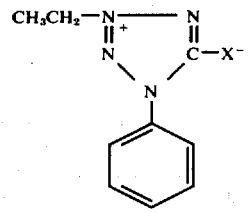

wherein X$^-$ is selected from -S$^-$ and -Se$^-$.

The aforementioned 3-ethyl-5-methylthio-1-phenyltetrazolium fluoroborate comprising the novel intermediate useful in producing the above-defined meso-ionic compounds may be represented by the formula

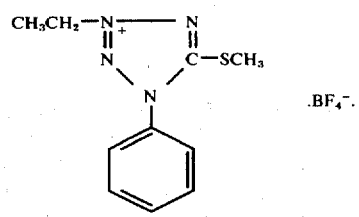

In preparing the subject tetrazolium fluoroborate, one molar equivalent of 5-methylthio-1-phenyltetrazole is reacted with about one molar equivalent of triethyloxonium fluoroborate in dichloromethane solution at a temperature of between about 15° and 40° C. The 5-methylthio-1-phenyltetrazole starting material may be prepared in a known manner by methylation of 5-mercapto-1-phenyltetrazole, for example, by reaction with methyl iodide.

To synthesize the subject meso-ionic compounds, the 3-ethyl-5-methylthio-1-phenoltetrazolium fluoroborate is reacted with sodium hydrogen selenide in aqueous alkanol solution at a temperature of between about 0° and 10° C. giving the selenium-containing meso-ionic compound defined above, which presumably is formed by nucleophilic attack by SeH$^-$ with the loss of methanethiolate anion. Treatment of the 3-ethyl-5-methylthio-1phenyltetrazolium fluoroborate with sodium hydrogen sulfide gives the sulfur analogue. In the latter reaction, the temperature is between about 0° and 10° C. and is conducted in alkanol solution. The tetrazolium fluoroborate is reacted with about two molar equivalents of the sodium hydrogen selenide and of the sodium hydrogen sulfide. The alkanol employed is usually a lower alkanol containing 1 to 4 carbon atoms and generally is methanol or ethanol.

The following examples illustrate the preparation of compounds within the scope of this invention and are given for purposes of illustration only.

EXAMPLE 1

Preparation of

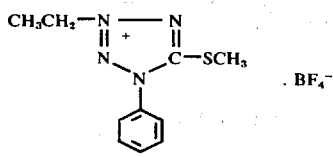

A solution of triethyloxonium fluoroborate (14.2 g.; 0.075 mol.) in anhydrous dichloromethane (105 ml.) was prepared in a glove bag under dry nitrogen. This solution was added dropwise to a stirred solution of 5-methylthio-1-phenyltetrazole (14.4 g.; 0.075 mol.) in anhydrous dichloromethane (100 ml.) at room temperature, and the resulting mixture stirred with exclusion of moisture for 7 days. The crystalline precipitate which had appeared was collected, redissolved in dichloromethane, and reprecipitated with ether, giving 9.9 g. of the title compound as a white solid, m.p. 155°–155.5° C.

Analysis for $C_{10}H_{13}BF_4N_4S$:

|  | C | H | B | F | N | S |
|---|---|---|---|---|---|---|
| Calculated | 38.98 | 4.25 | 3.51 | 24.66 | 18.18 | 10.41 |
| Found | 39.05 | 4.28 | 3.52 | 24.37 | 18.36 | 10.33 |

The filtrate from the foregoing product on dilution with ether gave further solid which was collected, redissolved in dichloromethane, and reprecipitated with ether, giving 14.4 g. of a white solid, melting range 144°–148° C., which was identical (IR and $^1H$ nmr spectra) with the higher-melting material.

EXAMPLE 2

Preparation of

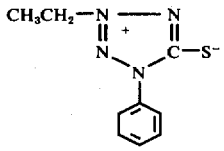

Sodium (313.6 mg., 13.64 mmoles) was dissolved in 50 mls. of methanol and the resulting solution cooled to 5° C. and saturated with $H_2S$ during 2.5 hours with stirring. Excess $H_2S$ was absorbed in an aqueous sodium hydroxide trap. A check valve and safety trap was placed between the sodium hydroxide trap and the apparatus, and another safety trap was placed between the apparatus and the hydrogen sulfide cylinder. 3-Ethyl-5-methylthio-1-phenyltetrazolium fluoroborate (1.85 gms., 6.00 mmoles) was then added slowly as a solution/slurry in 75 mls. of methanol during 0.5 hour while $H_2S$ was still being passed into the stirred solution. It should be noted that too rapid addition of the tetrazolium salt results in serious suck-back problems. After all the tetrazolium salt had been added, passage of $H_2S$ and stirring was continued for a further 0.5 hours, during which time the mixture came to room temperature. The $H_2S$ line was then disconnected and the mixture allowed to stir gently in a closed system overnight (about 16 hours). The resulting yellow solution was freed as far as possible from $H_2S$ by blowing $N_2$ through it, using a sodium hydroxide trap as before. After 2.5 hours the mixture was taken to dryness under reduced pressure (bath temperature—about 65° C.). Water was added to the yellow residue, whereupon most of the color went into solution, leaving a yellowish white crystalline solid, which was collected, washed well with water, air-dried and recrystallized from a mixture of 2:1 ethyl acetate: hexane (about 10 mls.) to give 0.90 g. of the title compound as faintly yellowish-white prisms (melting range 114.5°–115° C.).

Analysis for $C_9H_{10}N_4S$:

|  | C | H | N | S |
|---|---|---|---|---|
| Calculated | 52.35 | 4.93 | 27.20 | 15.37 |
| Found | 52.41 | 4.89 | 27.16 | 15.54 |

EXAMPLE 3

Preparation of

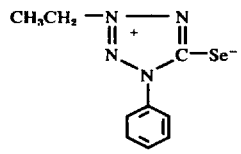

A system employing two flasks was set up wherein a solution of sodium bicarbonate (0.84 gm., 0.01 mmole) in 33 mls. of ethanol and 67 mls. water was placed in flask B and cooled to 0° C. in an ice bath with $N_2$ blowing through. Aluminum selenide (0.97 gm., 0.00335 mmoles) was weighted and crushed under paper in a mortar with a pestle. The system was clamped between flask A and the trap to flask B while the aluminum selenide was placed in flask A. The system was closed and unclamped and $N_2$ allowed to flow through the entire system for 30 minutes. The $N_2$ flow was then reduced to a bare minimum before generating $H_2Se$ by the addition of acid. 5 mls. of water and 13.2 mls. of 1.5N $H_2SO_4$ were placed in a dropping funnel and added dropwise to the aluminum selenide in flask A. After the addition, $H_2Se$ was observed to be bubbling into flask B. When the bubbling decreased, $N_2$ was passed through the system for about one hour at a rate to force the $H_2Se$ into the solution of flask B without forcing the $H_2Se$ out of the system before it could react. 3-ethyl-5-methylthio-1-phenyl tetrazolium fluoroborate (1.54 gms., 0.005 mmole) was dissolved in a solution of sodium bicarbonate (0.42 gm., 0.005 mmole) in 77 mls. of water and 35 mls. of ethanol. The resulting fluoroborate solution was filtered into a dropping funnel and added dropwise to flask B over a period of about one-half hour. The ice bath for flask B was kept at 0° C., and the fluoroborate solution added at a rate to maintain the reaction temperature between about 0° and 5° C. The resulting amber solution was stirred for 15 minutes before a pale yellow precipitate appeared. The mixture was allowed to stir in $N_2$ for 2 hours while coming to room temperature. The mixture was then allowed to stir in $N_2$ overnight (about 17 hours). Flask A was cooled to 0° C. and the solution therein decomposed by adding 25 mls. of 5N sodium hydroxide. After the decomposition was complete, flask A was detached from the system. Flask B was cooled to 0° C., and 9.5 mls. of 1.5N sulfuric acid was added dropwise to the solution in flask B. N₂ was passed through the solution for about one hour. A tan solid formed in the yellowish solution which was filtered in a nitrogen atmosphere, washed with water and dried under nitrogen, the solid was recrystallized in ethyl acetate:hexane to give 0.9 gm. of the title compound (melting range 128.5°–129° C.).

Analysis for $C_9H_{10}N_4Se$:

|  | C | H | N | Se |
|---|---|---|---|---|
| Calculated | 42.70 | 3.98 | 22.13 | 31.19 |
| Found | 42.70 | 3.93 | 22.02 | 31.07 |

The structures for the compounds prepared in Examples 2 and 3 above were assigned on the basis of the following U.V. and ¹³C nmr data.

| U.V. Spectral Data |||
|---|---|---|
| Solvent: 95% ethanol; conc.: 5 × 10⁻⁵ |||
| Compound | λ max(nm) | ε |
| Example 2 | 228 | 12,400 |
|  | 255 | 9,600 |
|  | 340 | 2,600 |
| Example 3 | 234 | 11,600 |
|  | 270 | 7,800 |
|  | 362 | 1,840 |
| 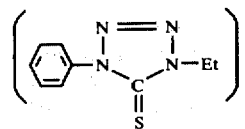 | 285 | 4,800 |
| 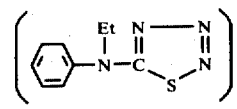 | 240 | 8,600 |
|  | 284 | 8,400 |

| U.V. Spectral Data ||
|---|---|
| Solvent: 95% ethanol; conc.: 5 × 10⁻⁵ ||
| Compound | λ max(nm) ε |
|  | 302    11,400 |

It will be apparent from reference to the above that the U.V. data indicates that the compound of Example 2 is not a thiatriazole, e.g., $$\left( \bigcirc\!\!-\!\!N\!\!\underset{C}{\overset{Et}{\underset{|}{N}}}\!\!\underset{S}{\overset{N=\!\!\!-N}{\underset{N}{\Vert}}} \right)$$

or a 1,4-disubstituted-5-thione $$\left( \bigcirc\!\!-\!\!N\!\!\underset{\underset{S}{\overset{\Vert}{C}}}{\overset{N=N}{\phantom{C}}}\!\!N\!\!-\!\!Et \right).$$

However, the U.V. data does indicate that the compounds of Examples 2 and 3 differ only in the substitution of Se for S.

¹³C NMR SPECTRAL DATA

All spectra were run on a Varian CFT-20 spectrometer (20 MHz). Unless otherwise stated, spectra were run in DMSO-d₆ solution at ambient temperature (about 35° C.), and with tetramethylsilane as internal reference. All chemical shifts are quoted relative to tetramethylsilane, downfield shifts being positive. All spectra of organoselenium compounds were run in the dark.

A. Effect of Substitution of Ring Sulfur by Selenium.

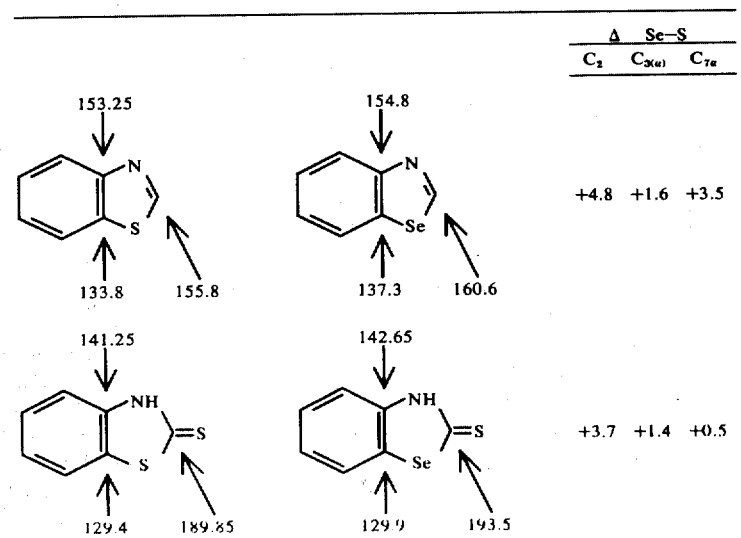

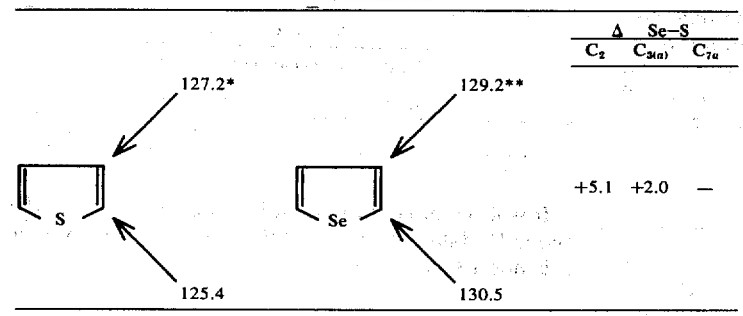

*T. E. Page, T. Alger, and D. M. Grant, J. Am. Chem. Soc., 1965, 87, 5333.
**F. J. Weigert and J. D. Roberts, J. Am. Chem. Soc., 1968, 90, 3543.

A deshielding effect of ring selenium is evident from the above comparison of benzoselenazoles and selenophene with the sulfur analogues. (As noted, the data on thiophene and selenophene are taken from the literature.) Specifically, it will be seen that the substitution of ring sulfur by selenium results in a marked downfield shift (3–5 ppm) at $C_2$. Also, it will be noted that the introduction of a thione function at $C_2$ of benzoselenazole decreases the deshielding effect of selenium at $C_{7a}$. It appears that mesomeric and diamagnetic anisotropy effects are the dominant factors in determining the effect of ring selenium in $^{13}C$ chemical shifts in these systems, as has been adduced for $^1H$ chemical shifts as discussed by U. Svanholm in "Organic Selenium Compounds: Their Chemistry and Biology," D. L. Klayman and W. H. H. Gunther, Eds., John Wiley & Sons, New York, N.Y., 1973, pp. 920–929.

B. Effect of Substitution of Selenium for Exocyclic Sulfur

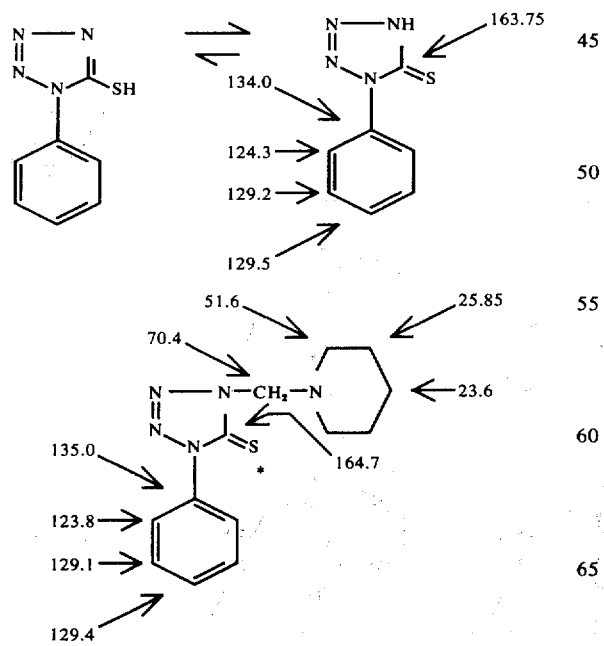

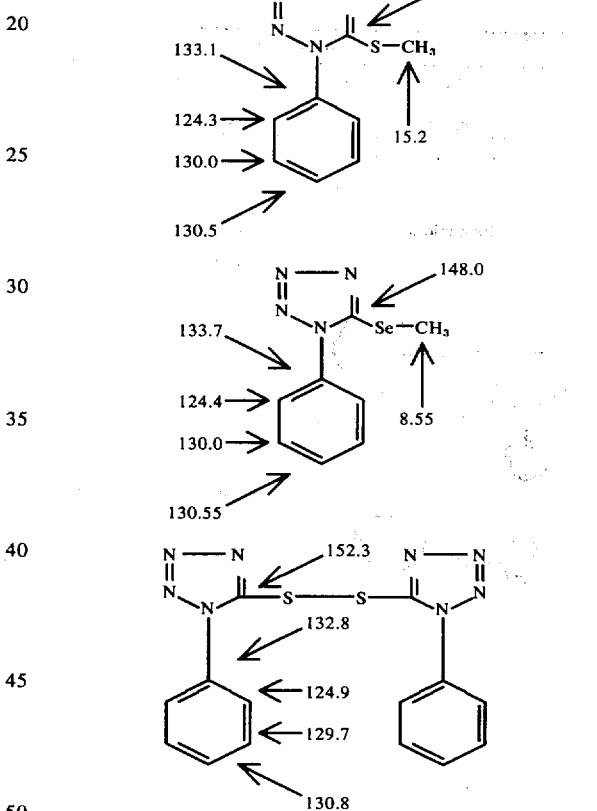

From the data set out above, it can be seen that 1-phenyltetrazole-5-thiol exists entirely as the thione tautomer, in agreement with the findings of Lieber, et al., Can. J. Chem., 36, p. 80 (1958). It will be noted that the chemical shift of the tetrazole carbon ($C_5$) comes close to that of 1-phenyl-4-(1'-piperidinomethyl)-$\Delta^2$-tetrazoline-5-thione, the structure of which has been established by the work of Postovskii and Nirenburg, Zhur. Obshch. Khim., 34, p. 2517 (1964). This latter compound was examined in chloroform-d solution owing to its insolubility in dimethylsulfoxide. However, the shifts being considered are much larger than normal solvent shifts in $^{13}C$ nmr. $C_5$ gives for the thio-ether a signal at 155.1 ppm and for the seleno-ether a signal at 148.0 ppm, giving $\Delta\delta_{Se-S} = -7.1$ ppm. The methyl resonances show an upfield shift of the same order, $\Delta\delta_{Se-S} = -6.6$ ppm. The tetrazole disulfide behaves like the thio-ether. It should be noted that recent work by L'abbe et al., J. Org. Chem., 39, p. 3770 (1974) on the $^{13}$C nmr spectra of 1-benzyl-Δ$^2$-tetrazoline-5-thione and its N- and S-substituted derivatives give values for C$_5$ chemical shifts that are very similar to those reported herein. The preparation of the tetrazole seleno-ether forms the subject matter of copending U.S. Patent Application Serial No. (Case 5396) of James R. Bartels-Keith.

On the basis of the data presented above regarding the effect of selenium on $^{13}$C chemical shifts, it can be seen that the substitution of exocyclic sulfur by selenium results in an upfield shift (shielding) at the carbon of attachment, whereas substitution of ring sulfur by selenium results in a downfield shift (deshielding).

C. Structure of Compounds of Examples 2 and 3 razoles, but very different from those of 5-anilino-1,2,3,4-thiatriazole despite the closeness of the thiatriazole C$_5$ signal (173.8 ppm) to the observed shift (173.5 ppm) in the compound of Example 2. Second, if the latter were a thiatriazole derivative, one would expect the selenium analogue of Example 3 to show the deshielding effect of ring selenium. The C$_5$ signal should appear around 178 ppm. Instead, on going from sulphur to selenium, one sees a strong shielding effect. Third, this shielding effect is almost exactly what one would expect for exocyclic selenium in the tetrazole series. In addition, comparison with the 1-phenyl-tetrazole-5-thiolate anion shows that the C$_5$ tetrazole resonance is shifted downfield on going from the latter to the meso-ionic N-ethyl derivative by an amount comparable with the deshielding effect observed on going

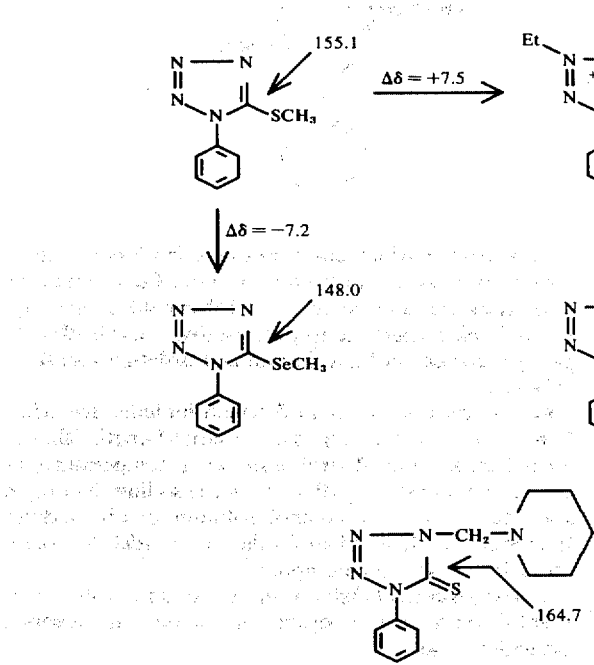

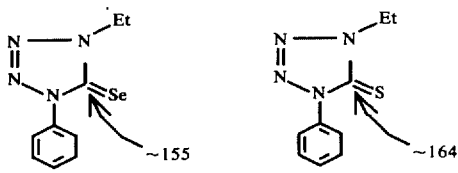

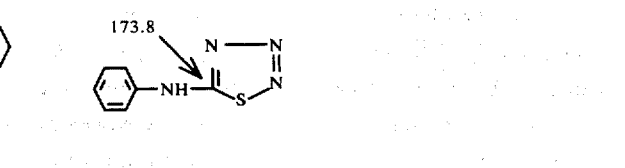

Predicted for 4-substituted compounds:

As will be seen from the above data, the C$_5$ chemical shifts measured for the compounds of Examples 2 and 3 were 165.8 and 173.5 ppm, respectively. These values are inconsistent with a 1,4-disubstituted selone (thione) structure, for which one would predict C$_5$ chemical shifts in the vicinity of 155 (selone) and 164 (thione) ppm based on correlations with the foregoing data. The U.V. spectra presented above support this conclusion, as well as indicating that these compounds are structural analogues, differing only in the chalcogen. The U.V. spectrum of 5 1,2,3,4-thiatriazole is quite different.

On the basis of the above $^{13}$C nmr and U.V. evidence, it is clear that the $^{13}$C shifts for the phenyl group in these materials are very like those of other 1-phenyltetfrom 5-methylthio-1-phenyl tetrazole to the 3-ethyl-5-methylthio-1-phenyltetrazolium cation. This effect is believed to be due largely to lowering of the electron density of the tetrazole ring. Also, the 1-phenyl group exerts a considerable steric effect at the 2-position as described by Lippmann et al., Z. Chem., 14, p. 16 (1974) in their studies on the acylation of tetrazole-5-thiols. Since the quaternization reactions are frequently quite sensitive to steric factors, this effect may be expected to operate in the ethylation of 5-methylthio-1-phenyltetrazole.

As noted previously, the meso-ionic compounds of the present invention are useful as photographic additives as illustrated by the following.

A photosensitive silver halide emulsion was exposed to a step wedge and processed by spreading a layer of processing composition approximately 1.2 mils. thick between the exposed emulsion and a superposed image-receiving element comprising a layer of regenerated cellulose containing colloidal palladium sulfide carried on a transparent support. The processing composition was prepared by adding the compound of Example 2 in a concentration of 1% by weight to the following formulation:

| | |
|---|---|
| Water | 814.0 g. |
| Uracil | 80.0 g. |
| Potassium hydroxide (Aqueous 50% w/w solution) | 348.0 g. |
| Hydroxyethyl cellulose | 35.0 g. |
| Zinc acetate | 15.0 g. |
| Triethanolamine | 5.6 g. |
| Tetramethyl reductic acid | 50.0 g. |

After an imbibition period of approximately one minute, the negative was separated from the image-receiving element, and the maximum and minimum transmission densities were measured for the positive image. The maximum density obtained was > 3.20 and the minimum density approximately 1.0. A control that was prepared in the same manner, except that the compound of Example 2 was omitted, gave a $D_{max}$ of 3.00 and a $D_{min}$ of 0.7. In addition to increasing the density of the silver transfer image, the compound of Example 2 was observed to improve the tone of the transfer image from brownish to slightly purplish-black.

The above procedure was repeated with the compound prepared in Example 3, and similar results were obtained.

Since certain changes may be made in the above compositions and processes without departing from the scope of the invention herein involved, it is intended that all matter contained in the above description should be interpreted as illustrative and not in a limiting sense.

What is claimed is:

1. A compound of the formula

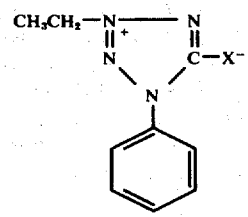

wherein $X^-$ is $-S^-$ or $-Se^-$.

2. The compound of claim 1 wherein $X^-$ is $-S^-$.
3. The compound of claim 1 wherein $X^-$ is $-Se^-$.
4. The compound

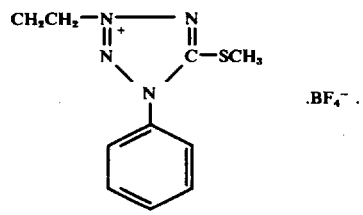

5. A process which comprises reacting 5-methylthio-1-phenyltetrazole and triethyloxonium fluoroborate at a temperature of between about 15° and 40° C. in anhydrous dichloromethane to yield 3-ethyl-5-methylthio-1-phenyltetrazolium fluoroborate and isolating said fluoroborate.

6. The process of claim 5 which includes the additional step of reacting said 3-ethyl-5-methylthio-1-phenyltetrazolium fluoroborate at a temperature of between about 0° and 10° C. with (a) sodium hydrogen selenide in aqueous alkanol solution or (b) sodium hydrogen sulfide in alkanol solution to yield the corresponding meso-ionic compound.

7. The process of claim 6 wherein said fluoroborate is reacted with sodium hydrogen selenide in aqueous ethanol solution.

8. The process of claim 6 wherein said fluoroborate is reacted with sodium hydrogen sulfide in methanol solution.

* * * * *